United States Patent [19]

Sianesi et al.

[11] 4,093,648
[45] June 6, 1978

[54] THERAPEUTICALLY ACTIVE BENZOIC ACID DERIVATIVES AND A PROCESS FOR PREPARING THEM

[75] Inventors: Enrico Sianesi, Milan; Giuseppe Bonola, San Donato Milan; Ivo Setnikar, Milan; Maria José Magistretti, Milan, all of Italy

[73] Assignee: Recordati S.A. Chemical and Pharmaceutical Company, Chiasso, Switzerland

[21] Appl. No.: 697,154

[22] Filed: Jun. 17, 1976

[30] Foreign Application Priority Data

Jul. 16, 1975  Italy ............................... 25448 A/75

[51] Int. Cl.$^2$ ..................... C07C 65/08; A01N 9/24
[52] U.S. Cl. .................. 260/519; 260/558 P; 260/559 S; 424/309; 424/324
[58] Field of Search ............... 260/519, 471 R, 471; 560/42

[56] References Cited

U.S. PATENT DOCUMENTS

| 2,847,344 | 8/1958 | Clinton et al. ............... 260/471 R |
| 2,872,476 | 2/1959 | Melkonian et al. ........... 260/471 R |
| 2,914,552 | 11/1959 | Hiltmann et al. ............. 260/471 R |

FOREIGN PATENT DOCUMENTS

| 203,001 | 4/1959 | Austria ............................. 260/471 R |

OTHER PUBLICATIONS

Moore et al., J.A.C.S., vol. 78, pp. 5633–5636 (1956).

*Primary Examiner*—Bernard Helfin
*Assistant Examiner*—James H. Reamer
*Attorney, Agent, or Firm*—Stevens, Davis, Miller & Mosher

[57] ABSTRACT

Therapeutically active 2- and 3-substituted benzoic acid derivatives having the general formula

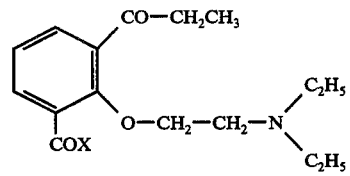

wherein X is OH, NH$_2$ or an anilino group having the phenyl ring unsubstituted or substituted by chlorine or by a 4-ethoxy group; or

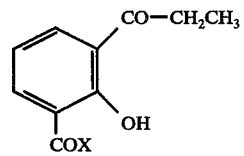

wherein X is NH$_2$ or an anilino group having the phenyl ring unsubstituted or substituted by chlorine or by a 4-ethoxy group; pharmacologically acceptable mineral or organic acid addition salts including quaternary ammonium salts of those compounds having a basic nitrogen atom and alkaline or alkaline earth metal salts of those compounds wherein X is OH.

Compounds of the formula wherein X is amino or anilino are prepared by reacting 3-propionylsalicyclic acid or a functional derivative thereof with ammonia or an amine in an anhydrous solvent. Compounds of the formula wherein X is OH are prepared by etherifying the ethylester of 3-propionylsalicyclic acid with diethylaminoethylchloride in the presence of an acid binding agent in a ketonic solvent and thereafter hydrolyzing the ester group with a mineral acid or an alkaline earth metal hydroxide.

3 Claims, No Drawings

THERAPEUTICALLY ACTIVE BENZOIC ACID DERIVATIVES AND A PROCESS FOR PREPARING THEM

This invention relates to new 2- and 3- substituted benzoic acid derivatives having the general formula

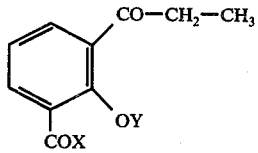

wherein Y is H (except when X = OH) or

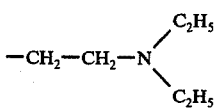

and X is OH (except when Y = H) or $NH_2$ or an anilino group having the phenyl group unsubstituted or substituted by a chlorine or by an ethoxy group and, for those compounds having a basic nitrogen atom, their pharmacologically acceptable mineral or organic acid addition salts including quaternary ammonium salts and, for those compounds wherein X represents OH, their alkaline or earth-alkaline salts.

The compounds of formula I and their pharmacologically compatible salts show antianaphylactic activity (which is rather remarkable for some of them) that may be successfully employed to prepare pharmaceutical formulations for human use against the allergic asthma and alimentary allergies. In order to evaluate the antianaphylactic activity, we have performed some comparison tests with sodium chromoglycate that is, at the present time, the most known and the most used antiallergic agent.

We wish to point out that some compounds of formula I are water soluble or become such by salification: therefore injectable solutions can thus be obtained. It is also worthy to note that these compounds keep their activity also when they are orally administered and that is an important advantage against chromoglycate that is inactive when administered per os.

The most active product of this series is the 2-diethylaminoethoxy-3-propionyl-benzoic acid, having the following formula

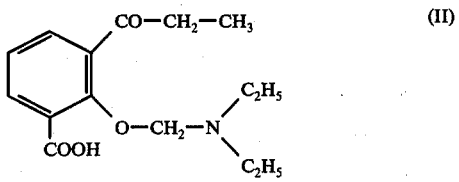

with which tablets, injectable solutions and aerosols have been prepared.

Starting products for the preparation of compounds of formula I are the 2-hydroxy-3-propionyl-benzoic acid (or 3-propionylsalicyclic acid) and its ethylester (both already described by us, for example in U.S. Pat. No. 3,770,802, in British Pat. No. 1,343,118, in Austrian Pat. Nos. 302,343 and 302,280 and so forth) having the formulae

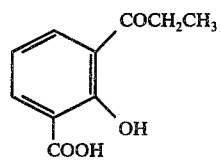

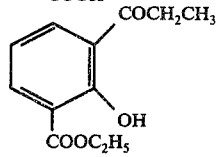

The processes for preparing compounds of general formula I are known methods.

So, for preparing compounds wherein X is an aminogroup, the 3-propionyl salicyclic acid of formula III or a functional derivative thereof (such as the chloride) is reacted in an anhydrous solvent (such as chloroform or benzene) with the appropriate amine, thereafter, if desired, the amide, prepared as described below, is reacted with diethylaminoethylchloride in the presence of an acid binding agent such as $K_2CO_3$ in a ketonic solvent. For preparing compounds wherein X is OH, the ethylester of the 3-propionylsalicyclic acid (compound of formula IV) is first etherified with diethylaminoethylchloride as previously described, thereafter the ester linkage is broken down by hydrolysis by means of a mineral acid or of an alkaline earth metal hydroxide, such as barium hydroxide.

For preparing acid addition salts and quaternary ammonium salts of the compounds of formula I having a basic nitrogen atom and for preparing alkaline or alkaline earth metal salts of those compounds of formula I wherein X = OH, the obvious processes are employed.

The processes that have been briefly mentioned, are described in detail in the following examples. Examples marked with capital letters relate to the starting products; those marked with a figure relate, on the contrary, to the compounds of general formula I.

EXAMPLE A

2-Hydroxy-3-propionylbenzoic-acid or 3-propionylsalicylic Acid

It is prepared by oxidization of the corresponding aldehyde by alkaline melting by the process described in U.S. Pat. No. 3,770,802.

EXAMPLE B

2-Hydroxy-3-propionylbenzoic acid ethylester or 3-propionylsalicylic Acid Ethylester It is prepared by esterifying 3-propionylsalicylic acid by the process described in U.S. Pat. 3,770,802.

EXAMPLE 1

3-Propionylsalicylamide (Form. I : X = $NH_2$; Y = H;)

A mixture of 3.88 g of 3-propionylsalicylic acid (see Ex. A), 16 ml of anhydrous toluene and 3.39 g of thionyl chloride is heated on a water bath until the gas development has ceased (1.5–2.0 hours) and kept cold overnight.

The solid, which is separated, is filtered, washed with a little toluene and dried under vacuum at room temperature over calcium chloride: 3.48 g of 3-propionylsalicyloyl chloride, as a yellow solid melting about 110° (empty tube) are obtained.

Into a solution of 2.12 g of 3-propionylsalicyloyl chloride in 100 ml of anhydrous chloroform, a stream of dried gaseous ammonia is bubbled for 30 minutes, by keeping the mixture moisture-free. From the chloroform solution, the product is water extracted and the aqueous solution acidified with concentrated HCl. After cooling (2 hours) the precipitate is collected and crystallized from methanol: yield 1.1 g m.p. 180°–182° C.

| Analysis for | $C_{10}H_{11}NO_3$ | | |
|---|---|---|---|
| | C% | H% | N% |
| calculated | 62.17 | 5.74 | 7.25 |
| found | 62.27 | 5.72 | 7.25 |

EXAMPLE 2

2-Hydroxy-3-propionyl (4-ethoxyphenyl)benzamide.

(Form. I:

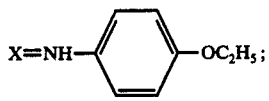

Y = H;)

A solution of 3.28 g of p-phenethidine in 10 ml of anhydrous chloroform is slowly added, under stirring and cooling in ice, to a solution of 2.12 g of 2-hydroxy-3-propionylbenzoyl chloride (Example 1) in 50 ml of anhydrous chloroform. The mixture is let stand 20 hours at room temperature, it is washed with 2N HCl, NaHCO$_3$ solution, water, then it is dried (Na$_2$SO$_4$) treated with charcoal, filtered and evaporated under vacuum; the solid yellow residue, by crystallization from 95% ethyl alcohol, yields 1.97 g m.p. 123°–125° C.

| Analysis for | $C_{18}H_{19}NO_4$ | | | |
|---|---|---|---|---|
| | C% | H% | N% | OC$_2$H$_5$% |
| calculated | 69.0 | 6.11 | 4.47 | 14.38 |
| found | 69.24 | 6.15 | 4.86 | 14.56 |

EXAMPLE 3

2-Hydroxy-3-propionyl (o-chlorophenyl) benzamide (Form. I:

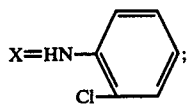

Y = H)

It may be prepared by the process described in Example 2.

Yellow solid m.p. 166°–167° C.

| Analysis for | $C_{16}H_{14}ClNO_3$ | | | |
|---|---|---|---|---|
| | C% | H% | N% | Cl% |
| calculated | 63.27 | 4.65 | 4.61 | 11.67 |

| Analysis for | $C_{16}H_{14}ClNO_3$ | | | |
|---|---|---|---|---|
| | C% | H% | N% | Cl% |
| found | 63.57 | 4.32 | 4.82 | 11.54 |

EXAMPLE 4

2-Hydroxy-3-propionyl (m-chlorophenyl) benzamide (Form. I:

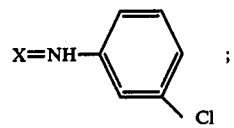

Y = H)

It may be prepared by the same process described in Example 2; pale yellow solid m.p. 159°–161° C.

| Analysis for | $C_{16}H_{14}ClNO_3$ | | | |
|---|---|---|---|---|
| | C% | H% | N% | Cl% |
| calculated | 63.27 | 4.65 | 4.61 | 11.67 |
| found | 63.41 | 4.62 | 4.87 | 11.64 |

EXAMPLE 5

2-Hydroxy-3-propionyl (p-chlorophenyl)benzamide (Form. I:

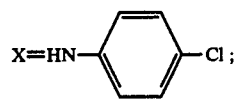

Y = H)

It may be prepared by the process described in Example 2; yellow solid m.p. 177°–178° C.

| Analysis for | $C_{16}H_{14}ClNO_3$ | | | |
|---|---|---|---|---|
| | C% | H% | N% | Cl% |
| calculated | 63.27 | 4.65 | 4.61 | 11.67 |
| found | 63.29 | 4.40 | 4.60 | 11.66 |

EXAMPLE 6

2-Hydroxy-3-propionyl-phenylbenzamide (Form. I: X = —HN—C$_6$H$_5$; Y = H)

It may be prepared by the process described in Example 2; yellow crystals m.p. 136°–137° C.

| Analysis for | $C_{16}H_{15}NO_3$ | | |
|---|---|---|---|
| | C% | H% | N% |
| calculated | 71.36 | 5.62 | 5.20 |
| found | 71.55 | 5.39 | 5.25 |

EXAMPLE 7

2(β-diethylamino)ethoxy-3-propionylbenzoic Acid (Form. I: X = OH; Y = CH$_2$CH$_2$—N(C$_2$H$_5$)$_2$)

Compound I - 2(β-diethylamino)ethoxy-3-propionylbenzoic acid ethylester hydrochloride (Form. I: X = OC₂H₅;

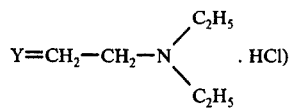

. HCl)

To a solution of 2.22 g of 3-propionylsalicylic acid ethyl ester (see EX. B) in 15 ml of anhydrous methylethylketone, 1.66 g of anhydrous potassium carbonate are added and the mixture refluxed by stirring for about 15 minutes: a soft yellow solid is formed. 1.63 g of 2-diethylaminoethylchloride are then added and the mixture is again refluxed for 1 h (after 45 minutes the soft yellow solid has disappeared and a heavy white solid is formed). After filtration the solvent is evaporated under vacuum and the oily residue is dissolved in ethyl ether. Ethereal solution is washed several times with water and then evaporated to dryness. The pale yellow oily residue is dissolved in 5 ml of ice-cooled 2N HCl and the solution is extracted with two portions each of 5 ml of chloroform. The chloroform is dried ($Na_2SO_4$) and evaporated under vacuum: the residue is taken up with 30 ml of anhydrous benzene and the solution again evaporated under vacuum.

The oily residue, treated with ethylether, slowly solidifies. Ether is decanted, the solid is dried under vacuum and over KOH and crystallized from ethyl acetate: yield 2.46 g m.p. 82°–85° C.

| Analysis for | $C_{18}H_{27}NO_4$ . HCl | | | |
|---|---|---|---|---|
| | C% | H% | N% | Cl% |
| calculated | 60.41 | 7.89 | 3.91 | 9.91 |
| found | 60.25 | 7.73 | 3.99 | 10.03 |

(A) 30 g of 2(β-diethylaminoethoxy)-3-propionylbenzoic acid ethylester hydrochloride (Compound I) dissolved in 150 ml of 2N HCl are refluxed taking care to remove by distillation the alcohol formed and to maintain the original volume of the liquid by addition of water; the solution is evaporated under vacuum and the residue is kept under vacuum in the presence of NaOH to remove the excess of HCl. 27 g of a pink solid consisting in the hydrochloride of the required compound, are obtained. After crystallization from acetone, 25 g of a white compound, which, after drying for 8 hours at 4 mm Hg over NaOH, melts at 111°–113° C, are obtained.

| Analysis for | $C_{16}H_{23}NO_4$ . HCl | | | |
|---|---|---|---|---|
| | C% | H% | N% | Cl% |
| calculated | 58.27 | 7.33 | 4.25 | 10.75 |
| found | 58.44 | 7.41 | 4.24 | 10.75 |

(B) The solution of 10 g of hydrochloride (see preceding Example A) in 80 ml of water is passed very slowly through a column (φ 2.5 cm) containing 25g of Relite MG1 in basic form, washing then the column with 60 ml of water. The liquid is then passed through another column (φ 1 cm) containing 7 g of Relite MG1 in basic form (a weak anionic exchange resin commercially available from Sybron Italia S.p.A., Resindion Division) and the column is washed lastly with 20 ml of water. The eluted liquid and the washings are combined and evaporated to dryness (bath temperature about 45° C) and the residue (9.3 g) is crystallized as described in C (see later). Yield 8.2 g; m.p. 103°–105° C (The compound, checked by thin layer chromatography, is unitary).

| Analysis for | $C_{16}H_{23}NO_4$ . $H_2O$ | | | |
|---|---|---|---|---|
| | C% | H% | N% | $H_2O$ |
| calculated | 61.22 | 8.09 | 4.50 | 5.79 |
| found | 61.75 | 8.16 | 4.29 | 5.60 |

(C) Into a three-necked flask equipped with a stirrer and protected from $CO_2$, 249 g of Ba $(OH)_2·8H_2O$ are suspended in 1860 ml of water. To this suspension a solution of 371 g of 2(diethylaminoethyoxy)-3-propionylbenzoic acid ethylester in 930 ml of methanol is quickly added under stirring. (The 2-(diethylaminoethoxy)3-propionyl benzoic acid ethyl ester is obtained by adding to an aqueous solution of the hydrochloride (Compound I) an excess of $K_2CO_3$, collecting the oil formed and extracting the mixture with a solvent). The temperature should be maintained under 21° C. The mixture is then stirred at room temperature (21°–24° C). After 4–5 hours the base dissolves and after 6–7 hours the reaction is ended. The solution is filtered and then the barium is precipitated by a vigorous current of $CO_2$ until the mixture is no more alkaline (after 30–45' pH is about 7). Precipitated barium carbonate is filtered by suction (40 g of carbon are added to render easier the filtration). The lightly cloudy liquid is slowly passed through a column (φ 5 cm) containing 370 ml of Relite CC in ammoniacal form (a weak carboxylic cationic exchange resin commercially available from Sybron Italia S.p.A., Resindion Division) and the Relite is then washed with 400 ml of water. The clear solution so obtained is evaporated to dryness under vacuum (bath temperature about 45° C). The solid residue is dissolved in 680 ml of 95% ethanol by heating 3–5' at a temperature of about 45° C, the solution is diluted with 1350 ml of ethyl acetate, treated with charcoal, filtered and further diluted with 6150 ml of ethyl acetate. By standing at room temperature the product starts to crystallize and after standing overnight at about 5° C and after a further cooling in the ice-salt mixture for 1 hour, the precipitate is collected: 270 g m.p. 103°–105° C (in a sealed tube). Mother waters are evaporated to dryness under vacuum (bath temperature about 45° C) and the solid residue is recrystallized again as previously described: 30 g of product are again obtained: m.p. 103°–105° C.

The two combined products are dried 8 hours at room temperature at a pressure of 0.4 mm Hg and then let stand 24 hours in the open air. Total yield: 300 g.

EXAMPLE 8

2(β-diethylamino)ethoxy-3-propionylbenzoic Acid Calcium Salt Dihydrate

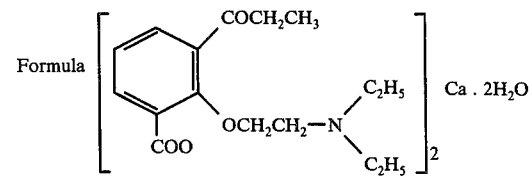

To a solution of 3.11 g of the 2(β-diethylamino-ethoxy)-3-propionylbenzoic acid monohydrate (see previous Examples B and C) in 30 ml of water, 0.37 g of calcium hydroxide are added. After a short time, a cloudy solution is obtained that is paper filtered and dried off over a water bath (at a temperature up to 40° C). The solid residue (3.44 g) is crystallized from methanol/ether, dried under vacuum at 50° C and then left in open air. 2.1 g of the dihydrate calcium salt of 2-(β-diethylamino)ethoxy-3-propionylbenzoic acid are obtained, m.p. 157°–158° C (after a change at about 95° C).

| Analysis for | $C_{32}H_{44}N_2O_8Ca \cdot 2H_2O$ | | | | |
|---|---|---|---|---|---|
| | C% | H% | N% | Ca% | $H_2O$% |
| calculated | 58.16 | 7.32 | 4.24 | 6.06 | 5.58 |
| found | 58.14 | 7.15 | 4.30 | 5.98 | 5.36 |

EXAMPLE 9

2(β-diethylamino)ethoxy-3-propionylbenzamide Hydrochloride (Form. I: $X = NH_2$;

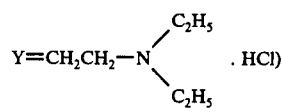

To a solution of 1.93 g of 3-propionylsalicylamide (Ex. 1) in 50 ml of anhydrous methylethylketone, 1.66 g of anhydrous $K_2CO_3$ are added under stirring and the mixture is then refluxed for 15 minutes. After having added the solution of 2.44 g of diethylaminoethylchloride in 30 ml of anhydrous methylethylketone the mixture is refluxed again for 16 hours. After cooling to room temperature, the undissolved solid is filtered, washed with methylethylketone and the filtrate evaporaed under vacuum. The oily residue is dissolved in 2N HCl, the solution filtered, alkalized with an excess of solid $K_2CO_3$ and extracted with ether. The ether extract is washed with water, dried ($K_2CO_3$) decolorized with charcoal and acidified with ethanolic HCl. A pink precipitate is formed which is crystallized from anhydrous acetone; yield 2 g of a white product m.p. 109°–113° C.

| Analysis for | $C_{16}H_{24}N_hd 2O_3 \cdot HCl$ | | | |
|---|---|---|---|---|
| | C% | H% | N% | Cl% |
| calculated | 58.44 | 7.66 | 8.52 | 10.78 |
| found | 58.73 | 7.76 | 8.45 | 11.04 |

EXAMPLE 10

2-Diethylaminoethoxy-3-propionyl-phenylbenzamide. HCl (Form. I: $X = HN—C_6H_5$;

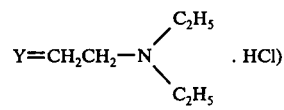

It may be prepared by the same process described in Example 9; white crystals m.p. 155°–157° C.

| Analysis for | $C_{22}H_{28}N_2O_3 \cdot HCl$ | | | |
|---|---|---|---|---|
| | C% | H% | N% | Cl% |
| calculated | 65.26 | 7.22 | 6.92 | 8.75 |
| found | 64.95 | 7.35 | 6.77 | 9.09 |

EXAMPLE 11

2-Diethylaminoethoxy-3-propionyl-(p-ethoxy)phenylbenzamide. HCl (Form. I:

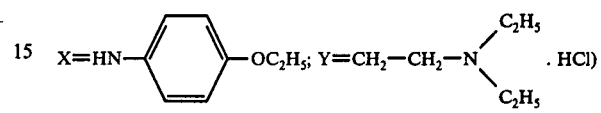

It may be prepared by the same process described in Example 9; white crystals m.p. 171°–173° C.

| Analysis for | $C_{24}H_{32}N_2O_4 \cdot HCl$ | | | |
|---|---|---|---|---|
| | C% | H% | N% | Cl% |
| calculated | 64.20 | 7.41 | 6.24 | 7.89 |
| found | 64.14 | 7.59 | 6.20 | 7.81 |

EXAMPLE 12

2-Diethylaminoethoxy-3-propionyl-(p-chlorophenyl)-benzamide. HCl (Form. I:

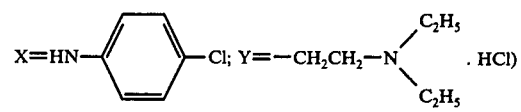

It may be prepared by the same process described in Example 9; white crystals m.p. 161°–164° C.

| Analysis for | $C_{22}H_{27}ClN_2O_3 \cdot HCl$ | | | |
|---|---|---|---|---|
| | C% | H% | N% | Cl% |
| calculated | 60.14 | 6.42 | 6.37 | 16.14 |
| found | 60.37 | 6.50 | 6.47 | 16.13 |

In the following table the biological data of some compounds of general formula I are reported.

The evaluation of biological data has been carried out by the most accepted test of the cutaneous passive anaphylaxis on the rat. We have followed the method described by J. Mota on Life Science 12,917 (1963) that was appropriately modified. The $LD_{50}$ determination was carried out with the common method, by administering intraperitoneally the compound to rats. The chromoglycate was used as a standard. In the first column, are listed the $LD_{50}$ values (mg/Kg), in the second the ratios $$\frac{\text{activity of the compound under test}}{\text{activity of chromoglycate}},$$

in the last column the ratios $$\frac{\text{therapeutic index of the compound under test}}{\text{therapeutic index of chromoglycate}}.$$

TABLE I
BIOLOGICAL DATA

| NO. | LD$_{50}$ | Compound activity / Standard activity | Compound therapeutic index / Standard therapeutic index |
|---|---|---|---|
| 2 | 3000 | 1.20 | 1.20 |
| 3 | 3000 | 1.19 | 1.19 |
| 7 | 3000 | 1.22 | 1.22 |
| 4 | 2700 | 1.12 | 1.00 |

Although the invention is described in detail for the purpose of illustration, it is to be understood that such detail is solely for that purpose and that variations can be made therein by those skilled in the art without departing from the spirit and scope of the invention except as it may be limited by the claims.

What is claimed is:

1. Therapeutically active 2- and 3-substituted benzoic acid derivative having the general formula

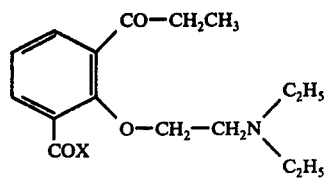

wherein X is OH and its alkaline or alkaline earth metal salts.

2. 2-diethylaminoethoxy-3-propionyl-benzoic acid.

3. Pharmaceutical preparations for human use containing the compound of claim 2 or its alkaline or alkaline earth metal salts, alone or compounded with other compatible drugs or with common excipients.